United States Patent [19]
Branum

[11] Patent Number: 5,182,817
[45] Date of Patent: Feb. 2, 1993

[54] GOGGLES HAVING AN EXTRUSION-MOUNTED LENS

[76] Inventor: Brian Branum, 1301 Willow Way, Garland, Tex. 75043

[21] Appl. No.: 729,483

[22] Filed: Jul. 12, 1991

[51] Int. Cl.⁵ .............................................. A61F 9/02
[52] U.S. Cl. ........................................ 2/439; 2/449
[58] Field of Search ................. 2/439, 429, 432, 434, 2/441, 443, 444, 447, 449, 450, 451, 453, 454, 426, 430, 427, 428, 431; 351/41, 47, 178

[56] References Cited

U.S. PATENT DOCUMENTS

| | | | |
|---|---|---|---|
| 2,920,327 | 1/1960 | Singer | 2/431 |
| 3,694,814 | 10/1972 | DeBarbieri et al. | 2/439 |
| 4,171,543 | 10/1979 | Cressi | 2/429 |
| 4,271,538 | 6/1981 | Montesi et al. | 2/439 |
| 4,547,909 | 10/1985 | Bell | 2/431 |
| 4,606,670 | 8/1986 | Angell | 2/429 |
| 4,976,530 | 12/1990 | Mackay et al. | 351/47 |
| 5,016,292 | 5/1991 | Rademacher | 2/448 |
| 5,027,443 | 7/1991 | Watkins | 2/441 |

FOREIGN PATENT DOCUMENTS

| | | | |
|---|---|---|---|
| 419854 | 4/1991 | European Pat. Off. | 2/449 |
| 514280 | 11/1939 | United Kingdom | 2/441 |
| 598136 | 2/1948 | United Kingdom | 351/41 |
| 2221551 | 2/1990 | United Kingdom | 2/431 |
| 9111159 | 8/1991 | World Int. Prop. O. | 2/426 |

Primary Examiner—Werner H. Schroeder
Assistant Examiner—Michael A. Neas
Attorney, Agent, or Firm—John M. Harrison

[57] ABSTRACT

Goggles having an extrusion-mounted lens, wherein the lens is mounted to the goggle frame using an extruded flexible member provided with a frame slot and a lens slot. In a preferred embodiment the lens slot and frame slot are parallel to each other and are sufficiently deep to removably mount on the inside edge of the frame and the outside edge of the lens and facilitate interchanging various lenses. Alternatively, glue may be applied to the frame slot and lens slot for permanently mounting the lens in the frame.

6 Claims, 1 Drawing Sheet

GOGGLES HAVING AN EXTRUSION-MOUNTED LENS

BACKGROUND OF THE INVENTION

Field of the Invention

This invention relates to goggles having temple pieces for alternate use and storage and more particularly, to goggles adapted to be worn both conventionally and fitted over conventional eye glasses and having an extrusion-mounted lens. In a preferred embodiment of the invention the goggle frame is provided with an extruded flexible plastic member fitted with continuous longitudinal frame and lens slots for receiving the inside edge of the frame and the outside edge of the lens and removably securing the lens to the frame. In this manner, various types of lenses, including polarized lenses, may be inserted in the lens slot and mounted in the frame, as desired. Alternatively, glue or cement may be applied to the frame slot and lens slot to permanently secure a particular lens in the frame, as desired. In each circumstance, the extruded lens mount serves to minimize scratching of the lens when the goggles are placed lens downwardly on a supporting surface and reduce damage to the lens due to shock, by acting as a shock absorber when the goggles are dropped on a hard surface and also to facilitate interchangeability of lenses, as desired. The lens mount further serves to improve the decorative effect of the goggles and may be provided in various colors to enhance this feature.

One of the problems associated with various types of goggles which are designed for wearing both with and without eye glasses is that of scratching the soft plastic lenses and the lack of interchangeability of shaded lenses, depending upon the brightness of the sun. While these lenses are normally highly resistant to impact, they are easily scratched and the frame may be easily broken by dropping on a hard surface such as concrete or the like, thereby rendering the goggles unfit for future use. Scratching of the lenses is a particularly bothersome problem since the plastic is normally easily scratched by any hard surface or even by careless cleaning. These conventional goggles also lack the facility for interchanging lenses, which may be necessary under circumstances where the outdoorsman is participating in a sporting activity indoors or in either bright sunlight or overcast conditions.

Various types of goggles are known in the art for use in sporting activities such as fishing, participating in active sporting events such as football and basketball and the like, as well as other purposes. Typical of these goggles is the custom-designed goggle used in active sports such as basketball, which goggles are constructed of a plastic frame and are fitted with non-tinted prescription lenses designed to correct the athlete's particular vision impairment. Other goggles are designed for fitting over eyeglasses and may be provided with polarized lenses having a desired degree of tinting to block the sunlight and provide better vision on bright, sunny days. These goggles are typically constructed with a plastic frame provided with a suitable lens and having folding temple pieces for easy storage.

It is an object of this invention to provide goggles having a removable or permanent extrusion-mounted lens for wearing by a user, either alone or over prescription glasses.

Another object of this invention is to provide goggles having extrusion-mounted lens that are removably mounted in the frame by means of a flexible lens mount attached to the frame and the lens.

A still further object of this invention is to provide goggles adapted for fitting over eye glasses and fitted with folding temple pieces and a tinted, polarized lens which is mounted in the frame by means of a flexible, extruded lens mount having continuous lens and frame slots for receiving the frame and

SUMMARY OF THE INVENTION

These and other objects of the invention are provided in new and improved goggles having temple pieces and adapted for wearing with and without eye glasses and further including extrusion-mounted, polarized lens, which lens are seated in a continuous lens slot provided in a flexible, elongated lens mount also having a frame slot for receiving the frame, to facilitate removably mounting the lens in the frame. Alternatively, a glue or cement may be applied to the frame slot and lens slot for permanently mounting the lens to the frame.

BRIEF DESCRIPTION OF THE DRAWING

The invention will be better understood by reference to the accompanying drawing, wherein.

DESCRIPTION OF THE PREFERRED EMBODIMENTS

Figure 1:
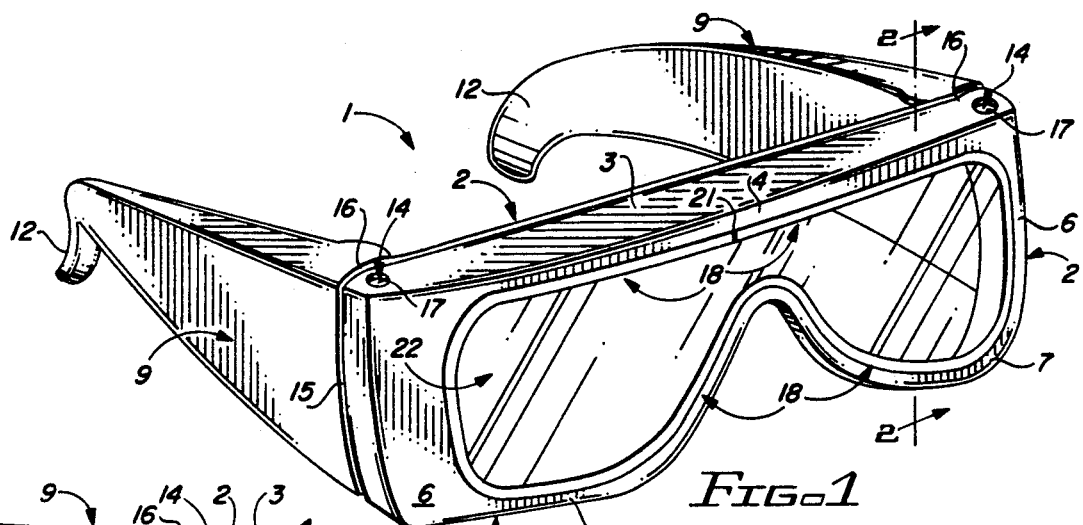
FIG. 1 is a front perspective view of a preferred embodiment of the goggles having an extrusion-mounted lens of this invention.
Figure 2:
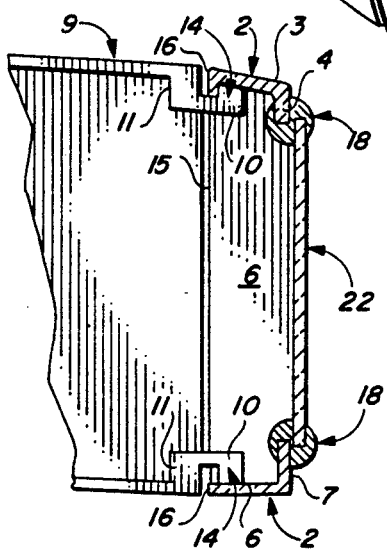
FIG. 2 is a sectional view taken along line 2—2 of the goggles illustrated in FIG. 1.
Figure 3:
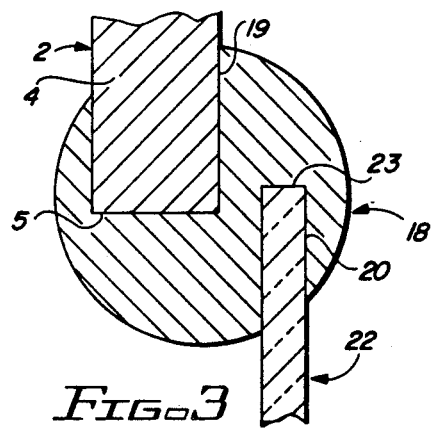
FIG. 3 is an enlarged sectional view of a typical lens mount, with the frame and lens inserted and mounted in corresponding frame and lens slots, in offset relationship, respectively.
Figure 4:
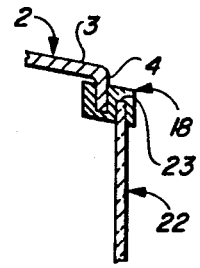
FIG. 4 is a side sectional view of an alternative preferred offset lens mount configuration.
Figure 5:
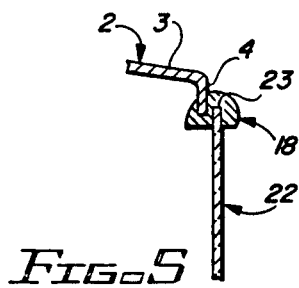
FIG. 5 is a sectional view of another alternative preferred offset lens mount configuration.
Figure 6:
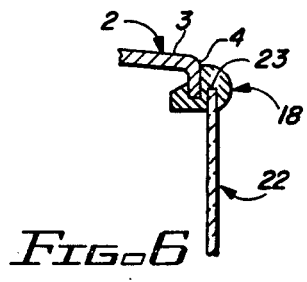
FIG. 6 is a sectional view of a third alternative preferred offset lens mount configuration.

Referring initially to FIGS. 1-3 of the drawing, in a preferred embodiment the goggles having an extrusion-mounted lens of this invention are generally illustrated by reference numeral 1. The goggles 1 are characterized by a lens frame 2 which is typically constructed of a plastic material such as cellulose acetate, butyrate or polycarbonate, by way of example. Other plastics, such as polyethylene, polypropylene and the like, in non-exclusive particular, may also be used to construct the lens frames 2, according to the knowledge of those skilled in the art. The lens frame 2 is characterized by a top segment 3, which defines a top segment leg 4 and a bottom segment 6, having an upwardly-extending bottom segment leg 7, as illustrated in FIGS. 1 and 2. A pair of temple pieces 9, also constructed of material such as cellulose acetate, butyrate, polycarbonate or other material as described above, are hingedly attached to the sides of the lens frame 2, as further illustrated in FIG. 2. This hinged relationship is effected by hinge mounts 10, extending from mount shoulders 11 of the tops and bottoms of each of the temple pieces 9 and corresponding hinges 14, which project into hinge openings 17, located in the top segment 3 and bottom segment 6 of the lens frame 2, as illustrated in FIGS. 1 and 2. Ear pieces 12 are shaped in the extending ends of each of the temple pieces 9 to facilitate wearing of the goggles 1 in conventional relationship or over eye glasses, as desired, with the ear pieces 12 engaging the ears of the user in conventional fashion. The temple pieces 9 are easily folded into a stored configuration (not illustrated) by operation of the respective hinges 14 and the folding clearance 15 and hinge clearance 16 between the temple pieces 9 and the lens frame 2, respectively, as further illustrated in FIG. 1.

Figure 9:
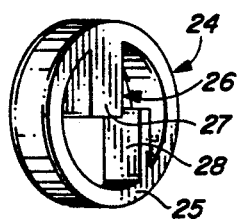
FIG. 9 is a perspective view of a typical die for extruding the lens mount illustrated in FIGS. 1-3.
Figure 7:
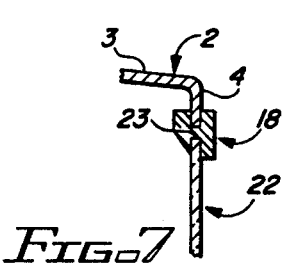
FIG. 7 is a sectional view of yet another lens mount configuration, wherein the frame and lens are inserted and mounted in the corresponding frame and lens slots in aligned relationship.
Figure 8:
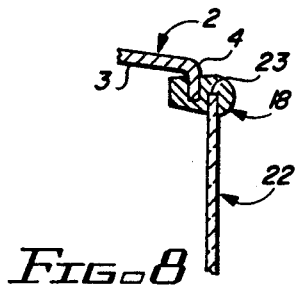
FIG. 8 is a side sectional view of still another alternative preferred offset lens mount configuration.

As illustrated in FIGS. 1-3 and 9, the flexible, extruded lens mount 18 may be constructed of rubber or other synthetic material which is sufficiently soft for mounting and yet sufficiently hard to retain its structural integrity and is inserted between the lens 22 and the lens frame 2, as hereinafter further described. In a preferred embodiment of the invention the lens mount 18 is fitted with a frame slot 19 and a lens slot 20, extended in parallel planes, in slightly overlapped relationship in the lens mount 18 by operation of the lens mount die 9, as illustrated in FIGS. 3 and 9. This configuration of the frame slot 19 and lens slot 20 is created by forcing a selected molten plastic or rubber material through the die throat 26 of the lens mount die 24, around the frame extruder 27 and lens extruder 28, extending from the die body 25 into the die throat 26. The configuration therefore facilitates insertion of the frame edge 5 into the frame slot 19 and the lens edge 23 into the lens slot 20 to removably mount the lens 22 in the lens frame 2 in offset relationship, as illustrated in FIGS. 1-3. This offset positioning of the respective segment legs and lens 22 in the corresponding frame slot 19 and lens slot 20 increases shear resistance in the lens mount 18, although an alternative aligned mounting of the segment legs and lens 22 can be effected in the lens mount 18, as illustrated in FIG. 7. The lens mount 18 is typically installed in the lens frame 2 and receives the lens 22 with the lens mount margin 21 marking the ends of the lens mount 18, as illustrated in FIG. 1.

Referring now to FIGS. 4-9 of the drawing, it will be appreciated by those skilled in the art that the lens mount 18 may be extruded or otherwise constructed in cross-sectional configurations other than the round configuration illustrated in FIGS. 1-3. Other variations of the cross-sectional configuration and offset-mounting of the lens mount 18 are illustrated in FIGS. 4-6 and 8, in non-exclusive particular. Accordingly, it will be recognized by those skilled in the art that other configurations not illustrated in FIGS. 1-8 of the drawings may be utilized in the lens mount 18 of this invention without departing from the spirit and scope of the invention.

It will be appreciated by those skilled in the art that the lens mount 18 and alternative variously shaped counterparts illustrated in the drawing may be constructed of a wide variety of flexible, resilient materials, including rubber or plastic materials, according to the knowledge of those skilled in the art. The chosen material must be sufficiently soft to facilitate easy manipulation during the mounting operation, yet sufficiently hard and resilient to maintain its structural integrity and withstand shock. The material must also resist thermal expansion and contraction, corrosion from oils such as suntan lotion and the like and thermal and ozone degradation. In another most preferred embodiment of the invention the lens mount 18 is constructed by extrusion from a material known as "Santoprene", a trademark of Monsanto Company. The particular "Santoprene" product which is ideally suited for the lens mount 18 is a 73 dirometer plastic product, which "dirometer" designation is an indication of hardness of the material. "Santoprene" is a thermoplastic material which may be easily extruded by operation of the lens mount die 24, illustrated in FIG. 9, to define the necessary frame slot 19 and lens slot 20 and serves to tightly, yet removably, secure the lens mount 18 to the lens frame 2 and support the lens 22 in the lens frame 2. The "Santoprene" lens mount 18 is typically extruded through the lens mount die 24 or other suitable die by an extrusion process well known to those skilled in the art, in order to construct a lens mount 18 of sufficient structural integrity and length to mount the lens 22 in the lens frame 2.

It will also be appreciated by those skilled in the art that the lens 22 may be retrofitted to existing goggles 1 by initially cutting an opening in the lens frame 2 by any suitable technique, which opening is sufficiently large to receive the lens 22 and the lens mount 18 and mount the lens 22 on the lens frame 2 using the lens mount 18, as heretofore described. Alternatively, the lens frame 2 of the goggles 1 may be specially constructed with an opening of sufficient size to achieve the same result, according to the knowledge of those skilled in the art.

Referring again to FIG. 1 of the drawings, it will be further appreciated by those skilled in the art that the lens 22 may be constructed in two pieces instead of one, under circumstances where a nose piece (not illustrated) is provided in the center of the lens frame 2 for additional structural integrity. The two segments of the lens 22 are then inserted, using two pieces of lens mount 18 in the same manner as that described above for a single length of lens mount 18.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. Goggles having an extrusion-mounted lens, comprising a frame having a viewing opening bordered by an inside edge, temple pieces carried by said frame in hinged relationship, a flexible, resilient extruded lens mount having a frame slot for removably receiving the inside edge of said viewing opening of said frame and a lens slot for removably receiving said lens and removably mounting said lens in said viewing opening of said frame, said frame slot and said lens slot provided in offset, substantially parallel planes in said lens mount and extending at leas to a plane bisecting said lens mount perpendicular to said parallel planes.

2. The goggles of claim 1 wherein said lens further comprises a polarized lens.

3. Goggles having an extrusion-mounted lens and adapted to fit over eyeglasses, comprising a frame constructed of a plastic material and having a viewing opening bounded by an inside edge; temple pieces carried by said frame in hinged relationship; an elongated, flexible lens mount having a substantially circular cross-section, a longitudinal frame slot located in a first chord of said circular cross section for receiving said inside edge of said frame; and a longitudinal lens slot extruded in a second chord of said circular cross section for receiving the edge of said lens and securing said lens in said viewing opening and wherein the plane of said first chord is substantially parallel to the plane of said second chord.

4. The goggles of claim 3 wherein said lens further comprises a polarized lens.

5. The goggles of claim 3 further comprising cement provided in said frame slot and said lens slot for permanently securing said lens mount to said inside edge of said frame and said edge of said lens in said lens slot.

6. The goggles of claim 5 wherein said lens further comprises a polarized lens.

* * * * *